United States Patent [19]

Fons

[11] Patent Number: 5,524,483
[45] Date of Patent: *Jun. 11, 1996

[54] METHODS FOR LOCATING OIL OR GAS DEPOSITS EMPLOYING EARTH SURFACE TEMPERATURES

[76] Inventor: Lloyd C. Fons, 14410 Cindywood, Houston, Tex. 77079

[*] Notice: The term of this patent shall not extend beyond the expiration date of Pat. No. 4,476,716.

[21] Appl. No.: 147,823

[22] Filed: Nov. 2, 1993

Related U.S. Application Data

[63] Continuation of Ser. No. 923,477, Aug. 3, 1992, abandoned.

[51] Int. Cl.$^6$ ..................................... E21B 47/06
[52] U.S. Cl. ............... 73/154; 374/112; 374/136; 374/137
[58] Field of Search ............... 73/154, 152; 374/112, 374/136, 137, 102, 45; 250/253

[56] References Cited

U.S. PATENT DOCUMENTS

| | | | |
|---|---|---|---|
| 3,217,550 | 11/1965 | Birman | 73/154 |
| 3,363,457 | 1/1968 | Ruehle et al. | 73/154 |
| 3,410,136 | 11/1968 | Johns et al. | 374/136 |
| 3,805,587 | 4/1974 | Sayer | 73/154 |
| 3,892,128 | 7/1975 | Smith, Jr. | 73/154 |
| 4,120,199 | 10/1978 | Mufti | 73/154 |
| 4,490,613 | 12/1984 | Brame | 250/253 |
| 4,517,458 | 5/1985 | Barringer | 250/253 |
| 4,607,963 | 8/1986 | Ulrickson | 374/137 |

*Primary Examiner*—Robert J. Warden
*Assistant Examiner*—Hien Tran

[57] ABSTRACT

A method for predicting the likelihood of encountering oil or gas deposits below a location and determining the areal extent and magnitude (economic value) of such deposit. The earth's surface temperature at selected points within a location is compared to the earth's surface temperature at a plurality of points in the surrounding geographic area to determine locations having anomalously low surface temperatures which are indicative of the presence of oil or gas deposits. Representative earth surface temperatures for all locations under consideration and reference temperatures in the geographic area are obtained, under similar ambient conditions, at points having similar topography, vegetative cover and surface features for minimizing extraneous factors which affect earth surface temperature, such that the earth surface temperatures may all be compared with each other to determine locations which have low earth surface temperatures, and therefore are more likely to have oil or gas deposits beneath them. The magnitude of the temperature difference between a location having low temperatures and the representative temperature for the geographic area as a whole is indicative of the thickness and area of an oil or gas deposit below the location.

37 Claims, 1 Drawing Sheet

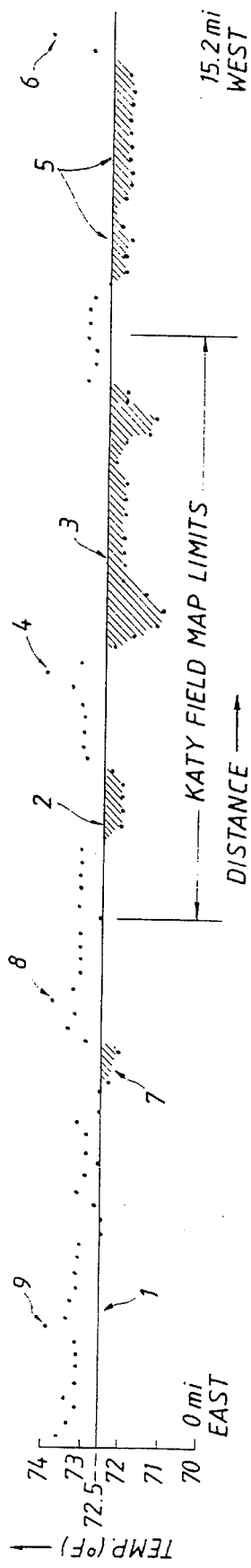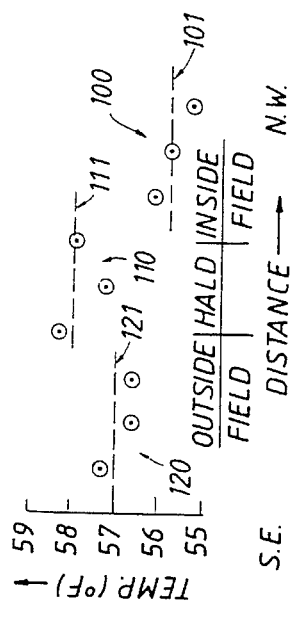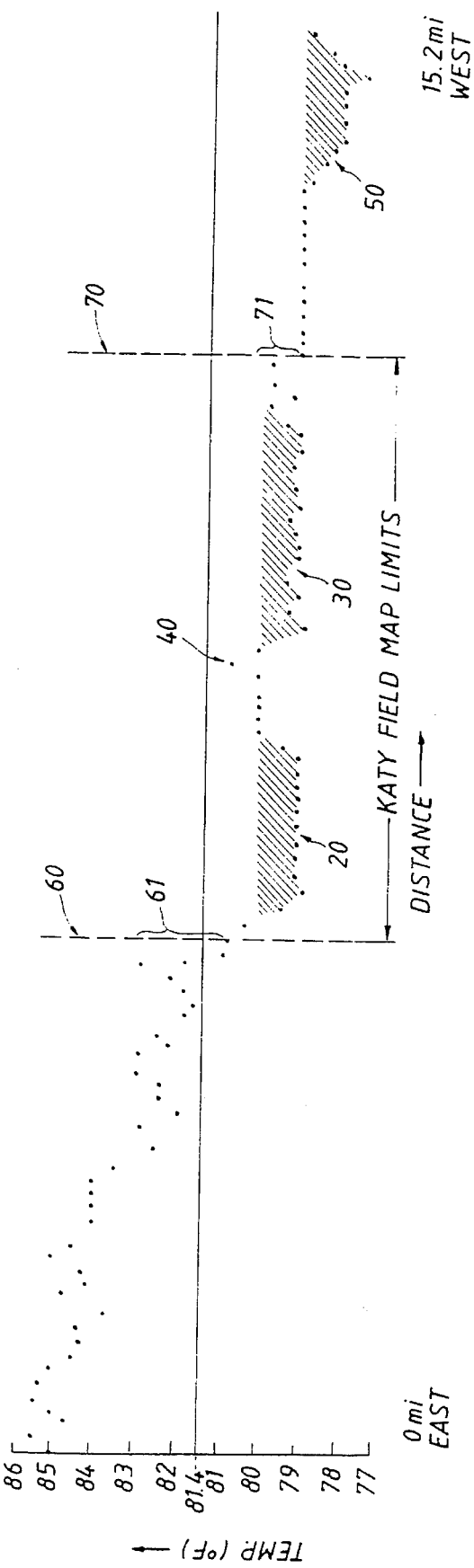

METHODS FOR LOCATING OIL OR GAS DEPOSITS EMPLOYING EARTH SURFACE TEMPERATURES

This is a Continuation of application Ser. No. 07/923,477, filed Aug. 3, 1992, now abandoned.

BACKGROUND OF THE INVENTION

1. Field of the Invention

The present invention relates to methods of exploring for oil or gas deposits. Particularly, the present invention relates to methods for predicting the likelihood of finding oil or gas deposits at unexplored depths beneath selected locations by utilizing earth surface temperatures. More particularly, the present invention relates to methods for predicting the likelihood that oil or gas deposits are present beneath selected locations by comparing the earth surface temperature at a selected location with earth surface temperatures in the surrounding geographic area. Anomalously low earth surface temperatures at a location indicate that oil or gas deposits are more likely to exist beneath that location than under locations with higher temperatures.

2. Description of Pertinent Art

In U.S. Pat. No. 4,476,716, incorporated by reference into this application in its entirety, I disclosed methods for predicting the likelihood that oil or gas deposits are present at unexplored depths below a selected location. These methods were based upon the discovery that temperatures at a given subsurface depth at a location above an oil or gas deposit tend to be lower than temperatures at the same depth at other locations in the same geographic area where oil and gas deposits do not exist. A principal method disclosed in U.S. Pat. No. 4,476,716 for predicting the likelihood that oil or gas deposits exist below a selected location comprises: determining an actual temperature ($T_a$) at a known depth beneath the location; determining an average temperature ($T_r$) for the known depth in the geographic area surrounding the location; and determining the temperature difference ($\Delta T = T_a - T_r$) between the temperature at the location and the average temperature, and predicting that oil or gas deposits are likely to be present below the known depth at the location for negative values of $\Delta T$, or predicting that oil or gas deposits are unlikely to be present below said known depth at said location for positive values of $\Delta T$.

In U.S. Pat. No. 4,476,716 it was observed that the surface of the earth, and very near-surface are affected by seasonal fluctuations in atmospheric and benthic temperatures, and at the near-surface depth to which seasonal temperature changes reach, the temperature of the earth is in many cases constant at about the value of the yearly average surface temperature. From this near-surface depth limit, the temperature of the earth begins its steady increase proportional to depth. Also, it was observed that temperatures and geothermal gradients for the same depth intervals vary significantly from well to well, even within small geographic areas. And finally, it was observed that temperatures at a first location above an oil or gas deposit tend to be lower than temperatures at corresponding depths at other locations, in the same geographic area with the first location, where oil or gas deposits do not exist.

Critical to the effectiveness of the methods in U.S. Pat. No. 4,476,716, is acquiring accurate subsurface temperature data such that temperature at a known depth below a selected location and average temperature for that depth in the geographic area surrounding the location are accurately known. As exemplified in claims 11 and 12 of U.S. Pat. No. 4,476,716, earth surface temperatures were believed to be affected by the presence or absence of oil or gas deposits below locations to such an extent that average annual atmospheric temperatures above such locations would be affected by a measurable amount. The magnitude of the difference in temperature between locations where oil or gas deposits do and do not occur increases from the surface to the depth just above where the oil or gas deposit is located. Thus, at the surface the temperature above an oil or gas deposit will be only slightly (but measurably) less than the average surface temperature for the geographic area. However, at a depth just above the oil or gas deposit, the temperature is much lower, often in the range of 40° F. to 60° F. lower, than the average temperature for such depth. The magnitude of the observable decrease in temperature above an oil or gas deposit is directly proportional to the size and thickness of the oil or gas deposit.

As exemplified in claims 11, 12 and 13 of U.S. Pat. No. 4,476,716, temperatures at particular locations, both in air and in water, are believed to be affected by the presence or absence of oil or gas deposits below the locations, and that sufficiently accurate temperature data (such as average annual atmospheric temperature data taken over many years) for particular locations and their surrounding geographic areas can be effectively used in the methods of U.S. Pat. No. 4,476,716 to predict the likelihood of oil or gas deposits existing below a particular location. Such average annual atmospheric (or benthic) temperature data is available for only a few locations, and is unavailable for the great majority of locations which are attractive sites for exploring for oil or gas. Collecting such average annual temperature data for even one location and its surrounding geographic area is prohibitively expensive. Collecting such average annual temperature data requires installation and monitoring of permanent temperature measuring installations at a number of places, including locations of interest, in the geographic area of interest for at least several years.

Surface temperature differences of significance in the search for oil or gas deposits are small. A large temperature deviation from average, in the range of 40° to 60° F., at the depth of an oil or gas deposit, will, when projected to the earth's surface, be reduced to a temperature deviation in the range of about ½° F. to 5° F., depending upon specific conditions at each location and geographic area measured.

Earth surface temperatures are affected not only by seasonal changes in temperature, but also by more immediate factors, such as diurnal effects, fluctuations in incident radiation (sunlight), ambient temperature, soil moisture, atmospheric humidity, wind desiccation, cloud cover, atmospheric clarity, precipitation, soil type, reflectance/emissivity of the surface, vegetative cover, elevation above/below sea level, local topography and surface features, etc. These factors tend to create temperature differences which mask any temperature differences between a location and its surrounding geographic area arising from the presence or absence of oil or gas deposits below the location. While time averages, such as average annual atmospheric temperatures, tend to eliminate the masking effect of these factors such that earth surface temperature effects due to the presence or absence of oil or gas deposits can be observed, obtaining such time average temperature data is not economically or functionally practical.

Consequently, a practical method for acquiring temperature data at the earth's surface and near-surface, which data is sufficiently accurate to show effects of the presence or absence of oil or gas deposits beneath the surface, are desirable for expanding the capacity for exploring for oil and gas reserves.

SUMMARY OF THE INVENTION

Now, according to the method of the present invention, I have discovered improved methods for predicting the likelihood that oil or gas deposits are present at unexplored depths beneath selected locations, which methods comprise acquiring earth surface temperature data and using the surface temperature data for predicting whether oil or gas deposits are present beneath a selected location.

BRIEF DESCRIPTION OF THE DRAWINGS

FIG. 1 is a graphical representation of a first set of temperature data collected according to the method of the present invention showing locations where oil or gas deposits are likely to be found.

FIG. 2 is a graphical representation of a second set of temperature data collected according to the method of the present invention showing locations where oil or gas deposits are likely to be found.

FIG. 3 is a graphical representation of temperature data collected according to the method of the present invention showing lower earth surface temperatures above a known deposit of oil and gas and showing a halo of higher temperatures at the edge of the known deposit of oil and gas.

DESCRIPTION OF PREFERRED EMBODIMENTS

In a preferred embodiment, the method of the present invention comprises:
  selecting a geographic area beneath which oil or gas deposits might be found;
  selecting points throughout the geographic area which have similar soil type, soil moisture, topography, vegetative cover and other surface features for minimizing the variability of earth surface temperature from point to point due to surface factors;
  selecting a time period, or periods during which ambient conditions, (for example, ambient temperatures, incident radiation, degree of cloud cover, precipitation, wind and atmospheric humidity and clarity) are similar throughout the geographic area for minimizing the variability of earth surface temperature from point to point due to such ambient conditions;
  measuring the earth surface temperature at each selected point in the geographic area during the selected time period;
  determining selected points which have low earth surface temperatures as compared with earth surface temperatures for other points within the geographic area; and
  predicting that selected points having comparatively low earth surface temperatures are more likely to have oil or gas deposits beneath them than are the selected points having comparatively high earth surface temperature.

According to the present invention, the earth surface temperature may be measured remotely, as with an infra-red sensor, or directly, with a temperature measuring device in physical contact with the earth.

When an infra-red sensor is employed to measure earth surface temperatures, it is desirable that the sensor be maintained at about the same elevation above and at about a 90° angle to the earth surface at each point to minimize the effect of variations in thickness of intervening atmosphere upon the measured temperatures. Preferably the sensor will be in sufficiently close proximity to the earth's surface that the moisture, haze, etc. of the intervening atmosphere will not have a substantial effect upon the temperature measurements obtained. Most preferably, the sensor will be within about one to four feet above and at substantially a 90° angle to the surface being measured.

Likewise, when temperature measurement devices used are in physical contact with the earth, the depth at which the temperature is measured at each point, from the actual surface to about the depth to which seasonal temperature changes penetrate, are preferably substantially the same at each selected point.

The advantages of economically and rapidly obtaining data over large geographic areas which can be used to predict locations which are likely to have oil or gas deposits beneath them offer great benefit to the oil and gas exploration industry. The potential of this benefit provided the impetus for the continued work which led to the discoveries of the present invention.

DETAILED DESCRIPTION OF THE INVENTION

Oil and gas deposits are commonly found in sedimentary earth formations from about the surface of the earth to depths of about 25,000 feet or more. Within these sedimentary formations it is known that the temperature of the earth steadily increases with depth from a point near the surface. In U.S. Pat. No. 4,476,716, it is disclosed that a subsurface temperature at a first location directly above an oil or gas deposit tends to be lower than temperatures at corresponding depths at other locations, in the same geographic area as the first location, where oil or gas deposits do not exist.

While not wishing to be bound by any theory of why temperatures vertically above oil or gas deposits are lower than average temperatures at corresponding depths for the geographic area, I have noted that the thermal conductivities of petroleum oil and natural gas are of substantially lower values than the thermal conductivities of materials, (limestone, sandstone, dolomite, shale, clay, sand, salty water, brine, anhydrite, and the like), commonly encountered in oil and gas wells. Thus, an oil or gas deposit may form an insulating blanket or layer which will retard the flow of heat from the interior of the earth to the surface. Accordingly, the temperature above an oil or gas deposit might be expected to be lower than the temperature at a comparable depth where no insulating layer of oil or gas is found. Such an insulating effect may form the basis for the phenomenon I have observed.

The methods of the present invention are based upon the observation that the lower subsurface temperatures of locations at depths near oil and gas deposits are in many cases continued, at reduced values to the earth's surface.

The surface and near-surface of the earth are affected by a variety of factors, including: seasonal atmospheric and benthic temperature changes; diurnal effects; local ambient conditions such as incident radiation, ambient temperature, atmospheric humidity, cloud cover, atmospheric clarity, precipitation, wind, soil moisture, etc.; and surface features such as elevation, grade, pooled water, soil saturation, surface reflectance/emissivity, vegetative cover and other topographical and surface features. Consequently, at the near-surface limit to which seasonal temperature changes reach (generally about the depth to which surface water will percolate) the temperature of the earth is in many cases constant at about the value of the average annual atmospheric temperature. From that depth to the surface, the earth temperatures fluctuate with seasonal and weather changes, while at the surface, earth temperatures are also affected by ambient conditions and diurnal effects.

Temperature lowering at the earth's surface attributable to the presence or absence of oil or gas deposits beneath locations is small. The temperatures at locations with oil or gas deposits beneath them are a few degrees or less (in the range of about ½° F. to 5° F.) lower than temperatures at locations with no oil or gas deposits.

In U.S. Pat. No. 4,476,716, I disclosed that temperature differences arising from the presence or absence of oil or gas deposits could be discerned at the surface in reported average annual atmospheric temperature data for various locations where such data has been collected. The averaging of the many individual temperature measurements over extended time periods required for obtaining the average annual atmospheric temperatures has the effect of statistically eliminating temperature variations due to atmospheric, diurnal and seasonal fluctuations. However, as stated above, gathering sufficient temperature data to calculate average annual temperatures at locations of interest for exploring for oil and gas deposits is much too expensive and time consuming for practical use.

According to the methods of the present invention, earth surface temperature measurements can be made at a plurality of points within selected locations in a geographic area rapidly and in a short time period when temperature fluctuations and variations due to seasonal, diurnal, ambient and topographical conditions are minimized and the temperature differences arising from the presence or absence of oil or gas deposits beneath selected locations in the geographic area can be measured directly.

The reference temperature for a geographic area is a temperature with which the representative temperature of a location is compared to determine whether the representative temperature of the location is low for the geographic area. The geological area reference temperature may be an average temperature, such as the arithmetic mean of the temperatures measured at all the selected points in the geographic area, or it may be an arbitrary temperature, such as the highest temperature measured, or the average annual temperature, or the mean temperature halfway between the highest and lowest temperatures measured.

Since the method of the present invention is particularly adapted to use in areas where very little or no subsurface control is available, such that, initially, a geographic area selected may have unrepresentative numbers of locations being likely to either have or not have oil or gas deposits beneath them. Consequently, the arithmetic mean of temperatures measured at all locations may be weighted to either the high or low end of the temperature range. In such cases one of the arbitrary temperatures may be selected as the reference temperatures against which temperatures for each location are compared.

When the average of the temperatures measured for all points is used as the geographic area reference temperature, then the location representative temperature may be compared directly to this average temperature. That is, if upon comparison the location representative temperature is seen to be lower than the average temperature, then the prediction can be made that the location is more likely to have an oil or gas deposit beneath it than is the geographic area as a whole.

When an arbitrary temperature is used as the geographic reference temperature, then the relation of the location representative temperature to the arbitrary temperature, and the relation of the temperatures at other points in the geographic area to the arbitrary temperature must be compared. That is, if the location representative temperature is lower than the arbitrary temperature by a greater amount than the temperatures at another selected point, then it can be predicted that it is more likely that an oil or gas deposit is beneath the location than beneath the other selected point and vice versa.

A geographic area will be sufficiently large to contain a plurality of locations, some of which are likely to have oil or gas deposits beneath, and some of which are likely not to have such deposits beneath them. The maximum size of a geographic area will be determined by the ability of a practitioner of the method of the present invention to measure temperatures throughout the geographic area during the time periods selected, as described below. Thus, a geographic area within contemplation of the present invention may be a small area comprising only a few locations, or maybe quite large, (perhaps of country or even state size). In selecting the geographic area, consideration will be given to having similar subsurface geology beneath the locations selected for study in the geological area. At least significant portions of the geographic area will have similar subsurface geology and similar surface features such that earth surface, or near-surface, temperature differences between selected locations within the geographic area have a likelihood of being due to the presence or absence of oil or gas deposits. As oil and gas deposits are commonly found in sedimentary earth formations, it is preferred that the geographic area selected comprise an area of sedimentary formations. Determination of subsurface geological features is the provenance of Geologists, and is made based upon surface features and outcrops in the geographic area and areas contiguous thereto, analysis of well logs which reveal subsurface structure and other means known to skilled Geologists.

A location, as contemplated herein is a smaller area within the larger geographic area where a well may be drilled if oil or gas deposits are predicted to lie below such location. Thus a location may comprise a point (such as where a stake is driven), or may be of some areal extent. The size of a location selected will be determined by a number of factors, including: the interests of the investigator, the method employed in accumulating temperature data, size of the geographic area relative to size of the location, expected areal extent of oil or gas deposits which may occur beneath a location, etc. Preferably, a location is compact enough to be not larger than the areal extent of any oil or gas deposit expected to be found beneath the location. Thus, depending upon the expected size of oil and gas deposits, the acceptable size range for locations may vary considerably. However, practically, a location may be considered to range in size from a single point, if only one temperature measurement is to be made per location, or may be considered to be larger, up to 1000 yards or so, if a plurality of temperature measurements are to be made and averaged for the location. All locations selected for study within the geographic area preferably have similar characteristics such as subsurface geology topography, surface features, and vegetative cover for the purpose of reducing the number of extraneous factors which affect earth surface temperatures between locations.

According to the present invention, locations having earth surface temperatures of lower value than earth surface temperatures at other locations with similar physical characteristics found in the same geographic area are likely prospects for having oil or gas deposits beneath them. Locations having higher earth surface temperatures are likely not to have oil or gas deposits beneath them. However, locations having anomalously high temperatures, compared to average or representative temperatures for the geographic area may represent the "halo" of higher temperatures sometimes found at the edge of oil or gas deposits, and may define the outer edge of an oil or gas field. Thus, anomalously high temperatures adjacent to a location of lower temperature contribute to the likelihood that oil or gas deposits exist below the location of lower temperature. Temperatures which are bout average for a geographic area are difficult to interpret, considering the small differences measured between the high and low temperatures. However, considering that temperatures are lower above larger deposits of oil or gas, it may be predicted that locations having about average or representative temperatures for the area do not have significant oil or gas deposits beneath them.

A point, as used herein, is a single spot on the earth's surface where the temperature is measured according to the method of the present invention.

Earth surface temperatures measured at the earth interface with the atmosphere point are unavoidably affected to some degree by a number of extraneous factors, as discussed above. Consequently, efforts are made to minimize the effect of these extraneous factors. Preferable points within the bounds of locations of interest and within the geographic area at large, are selected upon the basis of having similar subsurface geology and similar topography, vegetative cover and surface features for minimizing the effect of these extraneous factors upon the temperatures measured. Reducing the effect of the extraneous factors upon the measured temperatures aids in discerning the small differences in temperature arising from the presence or absence of oil or gas deposits beneath locations.

Surface features encompass many types of features which appear to effect the earth temperature, and generally vary substantially from point to point. It is desirable that surface features from point to point be similar to reduce their effect upon the variability of measured temperatures. Surface features to consider in selection of points include: elevation, grade, pooled water, soil saturation, soil types, surface reflectance/emissivity, vegetative cover and other topographical features. After elimination of points with gross differences in surface features, points are then selected upon the basis of having similar surface features. Visual inspection of points for similarity is generally sufficient. Roads, paved and unpaved, and bar ditches, where they exist, often provide extensive areas having similar surface features and topography which can be used to advantage as sources of temperature measurement points.

Other factors which affect earth surface temperatures are environmental factors such as temperature and diurnal changes, climatic changes, ambient temperatures, moisture content of the soil and of the atmosphere, precipitation, moisture evaporation due to radiation and wind desiccation, incident radiation (sunlight), and other weather conditions. These environmental factors are subject to rapid change. Consequently, to minimize the effect of these environmental factors, temperatures at the selected points are preferably all taken within selected time periods during which these environmental factors will remain fairly constant to reduce their effect upon the variability of temperature measurements. Preferably, a single time period during which these environmental factors will change little is selected for measurement of temperatures at all selected points within a geographic area. Sometimes this is not practical, and several time periods may be selected for measurement of temperatures at the selected points within the geographic area.

Temperature measurements, may be made at either the earth surface or at a near-surface depth below the surface. For evaluation of a location within a geographic area, temperatures at all selected points in the geographic area must be measured at the same depth. That is, all at the surface or all at a selected depth.

Near-surface temperatures are measured, according to the method of the present invention, at a selected shallow depth below the surface of the earth. To be within the disclosure of the present invention, the depth at which the temperature is measured is a depth equal to or less than the depth to which the seasonal climatic changes affect the earth temperature. Commonly, that depth is taken to be the depth to which surface water percolates into the earth. This depth however is quite variable, from about 0 on hard rock outcrops to tens of meters or more into porous soils, limestones, etc. Preferably, when the temperature is measured at a depth below the surface, the depth is sufficient to be beyond the immediate effect of incident radiation (sunlight), atmospheric temperature, and other surface conditions which may affect temperature measurement. Near-surface temperatures made at depths in the range of about one meter or more, are generally unaffected by diurnal changes. Time periods for measuring such near-surface temperatures can be relatively long, spanning days, for example. Such periods will ultimately end when seasonal climatic and temperature changes began to have an effect at the selected near-surface depth. Also, such time periods can be terminated or cut short by changes in ambient conditions, such as precipitation, desiccating winds, etc., which affect temperatures at the selected near-surface depth.

For surface temperature measurements, ambient conditions and diurnal factors have substantial effect. Consequently, time periods will preferably be of only several hours duration during each day when changes in ambient conditions and diurnal factors are minimum. Incident radiation (sunlight) has a very significant effect upon earth surface temperatures. Also, radiation of heat from the earth, particularly at night, has a significant effect. Consequently, when earth surface temperatures are being measured, time periods for taking such measurements are preferably when changes in incident radiation striking the earth and radiation leaving the earth are minimum. A preferred time period for taking earth surface temperature measurements is from about midnight, after most of the days heat has radiated off the earth, to before dawn, before incident radiation begins to increase. Cloudy conditions are preferred, because cloud cover reduces both the incident radiation striking the earth and radiation leaving the earth. Also, it is preferred that time periods be selected during seasons of the year when weather conditions such as temperature fluctuations, precipitation, wind, etc. will have least effect upon earth surface temperature.

Earth surface and near-surface temperatures may be measured with any instrument which provides sufficient precision and reproducibility, including instruments which physically contact the earth as well as remote sensing instruments.

Temperature measurements are preferably made to a precision of about $\frac{1}{4}°$ F. (or about $\frac{1}{10}°$ C.) or less. Temperature differences of as little as $\frac{1}{2}°$ F. will, in particular cases, be significant in determining whether oil or gas deposits are likely to be found beneath selected locations. Reproducibility of results is equally as important as precision. It is preferable that instruments employed in measuring the earth temperatures have no substantial drift, and that the instruments reproduce substantially the same measured value for repeated measurements of the same temperature. In the event instruments do have a drift such that repeated temperature measurements do not yield the same value, it is preferable that the rate of such drift is known and that measured temperatures be corrected for such drift before being used in the method of the present invention.

Examples of temperature measuring instruments which may be brought into physical contact with the earth to produce the desired temperature measurements are mercury thermometers, alcohol thermometers, bimetallic thermometers and thermocouples.

Examples of remote sensing instruments which may be used to obtain the desired temperature measurements are infra-red sensors. Preferably the infra-red sensors will be tuned to have heightened sensitivity to radiation at wavelengths generated by objects having temperatures in the range of the earth surface temperatures expected.

In the method of the present invention where earth surface temperatures are measured, use of remote sensing infra-red instruments are preferred. Temperature measurements can be made rapidly to a good precision with such instruments. Any drift, or lack of repeatability, in temperature readings obtained with infra-red sensors can generally be eliminated or compensated for by using a good quality sensor and following the manufacturer's operating instructions.

When earth surface temperatures are measured using remote sensing instruments such as infra-red sensors, it is preferable that the sensor be maintained at substantially the same distance, or elevation, above and at an angle of about 90 degrees to the earth surface at each point where a measurement is made for minimizing the effect of atmospheric conditions upon the temperatures measured. Atmospheric conditions such as relative humidity, moisture, fog, haze and so on have a substantial effect upon the temperature measured. The effect increases as the thickness of the atmosphere through which the measurement is made increases. Since atmospheric conditions, especially relative humidity and temperature of the air, can have a substantial effect upon temperature measurements made with infra-red sensors, it is preferable that such sensors be maintained in close proximity to the earth surface at the points where such temperature measurements are made. Distances above the surface of about 1 to 3 feet are preferable for ground based sensors, although greater or lesser distances may be used if conditions warrant. For air and space based sensors, care must be taken to minimize the effect of the atmosphere upon measured temperatures.

EXAMPLES

In order to demonstrate the present invention, the following experiments were performed. In these experiments, the area including and immediately surrounding the Katy Gas Field in the Texas Coastal Plain was chosen as the geographic area for study. The purpose of the experiments was to determine whether locations likely to have oil or gas deposits beneath them could be predicted using the methods of the present invention, and then verifying the predictions by comparison with the known boundaries of the Katy Gas Field.

For these experiments, an east-west traverse of the Katy Gas Field in the Texas Coastal Plain was established. The line of traverse was a straight east-west line about 15.2 miles long, established along a public road. This traverse line began well outside the known field boundaries on the east, crossed the field and ended well outside the known field boundaries on the west.

Example I

In this experiment, earth surface temperature measurements were made and recorded using an infra-red measurement instrument. The instrument used was an Omega Engineering Company, OS-82-LT Infra-red Thermometer, sensitive to infra-red radiation in the range of 8 to 14 Angstroms suitable for measuring temperatures in the range of −50° to 1700° F. The infra-red measurement instrument was mounted on the front bumper of an automobile about two feet above the road surface. The automobile was driven along the asphalt pavement of the road at a constant speed of 48.5 mph, completing the 15.2 mile traverse across the Katy Gas Field in 18 minutes, 49 seconds. The infra-red measuring instrument made and recorded a reading every second during the traverse, yielding 1129 temperature measurements for the 15.2 mile traverse.

In order to minimize the effect of any anomalously high or low temperature measurements caused by extraneous factors, each set of ten temperatures were arithmetically averaged to obtain a temperature representative of one location. Thus, 113 locations, each about 0.1448 miles long, were established along the 15.2 mile traverse.

The traverse to obtain the temperature measurements was made in late May, at 4:00 A.M. under conditions of no rain, cloudy overcast sky and atmospheric temperature of about 70° F. Under these conditions, the surface had maximum time during the night to equilibrate from solar radiation received during the previous day, and the road surface provided at each location a surface with minimum variation in ambient conditions from the surfaces at all other locations.

The results of this survey are shown in FIG. 1 of the drawings. In FIG. 1, the representative temperature for each location is plotted vs. its position along the traverse.

Each representative temperature is the arithmetic average of 10 temperature measurements made at one second intervals during the traverse, and thus represents the temperature of a location approximately 0.1448 miles long along the path of the traverse. The maximum representative temperature obtained was 74° F., and the minimum 71° F. Thus, the mean temperature of the geographic area (which is taken to be a narrow strip along the length of the traverse) is 72.5° F. In FIG. 1, this mean temperature is shown by line 1.

In FIG. 1, the approximate east-west limits of the Katy Field shown are obtained from publicly available maps. Examining FIG. 1, however, shows that two reservoirs, 2 and 3, appear to be within the field limits. The reservoirs are indicated by the locations having temperatures less than the mean temperature for the geographic area (72.5° F.).

Associated with the reservoir 3 is a high temperature anomaly of 74° F. indicated by numeral 4. This high temperature anomaly 4 may represent a high temperature halo around the edge of reservoir 3, and adds to the likelihood that an oil or gas deposit will be found below area 3. That gas deposits do lie below area 3 was confirmed later, in daylight, upon observing producing gas wells in area 3.

In FIG. 1, west of area 3 and outside the bounds of the Katy Field limits is an area of low temperature 5 which appears to be associated with an anomalously high temperature 6. The area 5 appears likely to have oil or gas deposits beneath as indicated by the low temperatures. The high temperature 6 may indicate a high temperature halo at the edge of an oil or gas deposit, and thus increases the likelihood that an oil or gas deposit does reside beneath area 5. Subsequently, in daylight, presence of producing wells south of the traverse, in line with area 5 appeared to confirm the presence of gas deposits beneath area 5.

In FIG. 1, a small area 7 of low temperature with anomalously high temperatures 8 and 9 on either side, suggests that oil or gas deposits may reside beneath area 7, and perhaps under the area east of area 7. Indications (low temperatures over significant area) are not so strong that a commercial deposit of oil or gas lies beneath area 7. However, the area may be worthy of further study, as it is possible that an oil deposit may lie below area 7. That is, while the low temperature area 7 is small for a gas deposit, it may indicate a significant oil deposit. No production history for area 7 could be located.

Example 2

This example was set-up similar to example 1. The traverse was over the same road using the same infra-red temperature measuring instruments attached to the front of the automobile about 2 feet above the road pavement. The automobile made the traverse at about 53 mph, and a temperature measurement was recorded each second. Each ten readings were averaged to obtain a representative temperature for each location along the traverse. Differences in conditions in example 2, compared to example 1, include, the traverse for example 2 was made in the day (12:30 P.M.) under a heavily overcast sky, in the rain, over a wet road. Examining FIG. 1 and FIG. 2 shows substantial difference in the temperature data obtained. Where Example 1 had a temperature span of 3° F., Example 2 had a span of about 8° F. Example 2 appeared to have distinctly higher temperatures in the east than in the west. However, closer examination of FIG. 2 shows some areas of agreement with data shown on FIG. 1. For example, area 20, high temperature 40, area 30 and area 50 are comparable to area 2, high temperature 4, area 3 and area 5 of FIG. 1. The absolute difference in temperatures (about 79° F. in example 2 vs. about 72° F. in example 1) may be explained by solar radiant heating in example 2. Other differences appear due to discontinuities at about positions 60 and 70, which could be explained as changes in solar radiation levels due to changes in cloud cover or precipitation rate. Thus, although information necessary for predicting whether oil or gas deposits are likely to be beneath locations in example 2, the information is fairly well obfuscated by the "noise" created by incident solar radiation.

Example 2 demonstrates that the effects of oil or gas deposits on surface temperatures survive the presence of strong extraneous effects upon temperature, such as solar radiation, and that such effects can be discerned, in the face of substantial noise, if data is properly analyzed. Also, Example 2 demonstrates the desirability of eliminating as many extraneous sources of temperature change as possible, so the data can be more easily analyzed to accurately predict the likelihood of oil or gas deposits being present beneath selected locations.

Example 3

In this Example, a traverse across the eastern edge of the Katy Gas Field was used. However, in this example temperatures were measured at a depth of about 3 feet below the earth's surface using a bimetallic thermometer. At each selected location along the traverse, a ⅜ inch hole about 3 feet deep was created by driving a rod into the ground along the soft shoulder of the road. The bimetallic thermometer, having a ¼ inch diameter stem three feet long, was placed in each hole where it remained for a period of about five minutes until the measured temperature reading stabilized. The temperature measurements ranged from a low of 55.9° F. to a high of 58.6° F., which represents a difference of only 2.7° F. These measurements were made in the month of February, and their low values, compared with the temperatures for the same area recorded in Examples 1 and 2, show the effect of seasons upon earth temperatures. Temperatures in Examples 1 and 2 were measured in the month of May.

Data obtained from this Example 3 is shown in FIG. 3. In FIG. 3, the traverse, from southeast to northwest, is shown along the abscissa, and temperature along the ordinate axis.

In FIG. 3, three temperature zones appear. Zone 100 is a low temperature zone having an average temperature of 56.2° F., as shown by line 101. Zone 120 is a medium temperature zone having an average temperature of 57.2° F., as shown by line 121. Finally, zone 110 is a high temperature zone having an average temperature of 58.2° F. as shown by line 111.

Zone 100 represents locations having low temperatures compared to other temperatures in the geographic area, and therefore, locations likely to have oil or gas deposits beneath them. This likelihood was confirmed by visual observation of producing gas wells adjacent the locations in zone 100.

Zone 120 represents locations having temperatures higher than the temperatures in zone 100. Therefore, according to the method of the present invention, locations in zone 120 are less likely to have oil or gas deposits beneath them than are locations in zone 100. This prediction was also confirmed by visual observation that no producing wells were seen near the locations in zone 120.

Zone 110 represents locations having temperatures which are anomalously high. Since zone 110 lies between zone 100 with known production nearby, and zone 120, without production nearby, this higher temperature of zone 110 appears to be a manifestation of the halo of high temperature which is reported to exist around the edge of oil or gas reservoirs.

These Examples demonstrate that, when the methods of the present invention are used, the temperature differences of one degree or less between locations in zone 100 and locations in zone 120 are sufficient to allow meaningful predictions of the likelihood that deposits of oil or gas will be found beneath selected locations. The required temperature data may be collected rapidly, especially when infra-red sensors are used, and large geographic areas may be evaluated for oil or gas production potential in a fast, efficient, and economical manner.

We claim:

1. A method for predicting the likelihood of the presence of oil or gas deposits beneath a location in a geographic area on the earth's surface, which method comprises:

a) selecting a geographic area on the earth's surface beneath which oil or gas deposits might be found;

b) selecting a location on the earth's surface within the geographic area;

c) selecting a time period during which temperature fluctuations and variations due to topographical, ambient, diurnal, and seasonal conditions are minimized;

d) during the selected time period, measuring an earth surface temperature at each of a first plurality of points in the geographic area;

e) calculating an arithmetic mean, (average), of the earth surface temperatures measured at the first plurality of points as a geographic area reference temperature;

f) during the selected time period, measuring an earth surface temperature at each of a second plurality of points within the location;

g) calculating the arithmetic mean, (average), of the earth surface temperatures measured at the second plurality of points as a location representative temperature;

h) comparing the location representative earth surface temperature to the geographic area reference temperature; and i) predicting that oil or gas deposits are more likely to be present beneath the location when the location representative surface temperature is lower than the geographic area reference temperature.

2. The method of claim 1 wherein the first and second plurality of selected points within the location and the geographic area have similar topography, vegetative cover and surface features for reducing the effect of extraneous surface conditions upon the measured earth surface temperatures.

3. The method of claim 1 wherein the earth surface temperature at each point of the first and second plurality of points is measured using an infra-red sensor maintained at substantially the same elevation above, and at about a 90° angle to, the earth's surface at each point of the first and second plurality of points.

4. The method of claim 3 wherein the infra-red sensor is maintained at a distance of about 1 to 4 feet above the earth's surface.

5. The method of claim 4 wherein spurious earth surface temperatures unduly affected by ambient conditions and/or extraneous surface conditions are discarded and not used in determining either the location representative temperatures or the geographic area reference temperature.

6. The method of claim 1 wherein the earth surface temperatures are measured using temperature measuring devices in physical contact with the earth's surface; and wherein the first and second plurality of points have similar topography, vegetative cover, and surface features for reducing the effect of extraneous surface conditions upon the measured earth surface temperatures.

7. The method of claim 3, wherein;

determining the geographic area reference temperature comprises measuring the earth surface temperature within the geographic area with an air based infra-red sensor; and determining the location representative temperature comprises measuring the earth surface temperature within the location with an air based infra-red sensor.

8. The method of claim 3, wherein;

determining the geographic area reference temperature comprises measuring the earth surface temperature with a space based infra-red sensor; and determining the location representative temperature comprises measuring the earth surface temperature with a space based infra-red sensor.

9. A method for predicting the likelihood of the presence of oil or gas deposits beneath one or more locations within a geographic area on the earth's surface, which method comprises:

a) selecting a geographic area on the earth's surface beneath which oil or gas deposits might be found;

b) selecting a plurality of points within the geographic area having similar topography, vegetative cover and surface features for reducing the effect of surface conditions upon earth surface temperatures at such points;

c) selecting a time period during which temperature fluctuations and variations due to topographical, ambient, diurnal and seasonal conditions are minimized;

d) measuring the earth's surface temperature at the selected points in the geographic area during the selected time period;

e) determining points of the plurality of selected points at which the measured earth surface temperatures are low compared to earth surface temperatures at other points of the plurality of selected points within the geographic area; and f) predicting that oil or gas deposits are more likely to be present beneath the points at which the measured earth surface temperatures are low compared to earth surface temperatures measured at the other points of the plurality of selected points.

10. The method of claim 9 including grouping selected points, which are adjacent to each other and have similarly low earth surface temperatures, for defining locations within the geographic area which are more likely to have oil or gas deposits beneath them.

11. The method of claim 10 including determining points, among the plurality of selected points, having anomalously high earth surface temperatures and which are adjacent to locations defined by groups of points, among the plurality of selected points, having low earth surface temperatures; and predicting that oil or gas deposits are likely to be present beneath locations defined by groups of points, among the plurality of selected points, having low temperatures and which are adjacent to points having anomalously high earth surface temperatures.

12. The method of claim 9 wherein the earth surface temperatures are measured using an infra-red sensor maintained at substantially the same elevation above, and at an angle of about 90°, to the earth's surface at each point of the plurality of selected points.

13. The method of claim 12 wherein the sensor is maintained at a distance in the range of about 1 to 4 feet above the earth's surface.

14. The method of claim 9 wherein the earth surface temperatures are measured using temperature measuring devices in physical contact with the earth.

15. A method for identifying locations suitable for exploring for oil or gas deposits, which method comprises:

a) selecting a geographic area beneath which oil or gas deposits might be found, and which comprises a plurality of locations;

b) selecting a time period during which temperature fluctuations and variations due to topographical, ambient, diurnal, and seasonal conditions are minimized;

c) determining, during the selected time period, an average earth surface temperature for each of the plurality of locations within the geographical area;

d) selecting, from the plurality of locations having determined average earth surface temperatures, locations having lower determined average earth surface temperatures than determined average earth surface temperatures of other of the plurality of locations, as locations suitable for exploring for oil or gas deposits.

16. The method of claim 15, including:

selecting as the time period, a time period during which ambient, diurnal and seasonal conditions are similar throughout the geographic area.

17. The method of claim 16, including:

determining the earth surface temperature for each of the plurality of location by measuring the earth surface temperature of each of the plurality of locations employing a sensor selected from the group consisting of air based and space based infra-red sensors maintained at about a constant elevation above, and at an angle of about 90° to the earth's surface.

18. The method of claim 16, including:

selecting as the plurality of locations, locations having similar surface features.

19. The method of claim 15, including:

measuring an earth surface temperature at each of a plurality of points in each of the plurality of locations during the selected time period; and employing an average of the earth surface temperatures at the plurality of points in each location as the average earth surface temperature for each location.

20. The method of claim 19, including:

selecting as the time period, a time period during which ambient, diurnal and seasonal conditions are similar throughout the geographical area.

21. The method of claim 20, including:

selecting points having similar surface features as members of the plurality of points in each of the plurality of locations.

22. The method of claim 20, including:

employing a temperature measurement instrument in physical contact with the earth's surface for measuring the earth surface temperature at each of the plurality of points in each of the plurality of locations.

23. The method of claim 22, including:

determining an average temperature value representative of the average of the average earth surface temperatures of the plurality of locations, and selecting locations, from the plurality of locations, having average earth surface temperatures lower than about the average temperature value of the plurality of locations, as locations suitable for exploring for oil or gas deposits.

24. The method of claim 20, including:

measuring the earth surface temperature at each of the plurality of points in each of the plurality of locations employing an infra-red sensor maintained at about a constant elevation above, and at an angle of about 90 degrees to, the earth's surface at each of said points.

25. The method of claim 24, including:

maintaining the constant elevation above the earth's surface in the range of about one to four feet.

26. A method for identifying locations suitable for exploring for oil or gas deposits, which method comprises:

a) selecting a geographical area beneath which oil or gas deposits might be found;

b) selecting a time period during which temperature fluctuations and variations due to topographical, ambient, diurnal and seasonal conditions are minimized;

c) measuring the earth surface temperature at each of a plurality of points within the geographical area during the selected time period;

d) selecting, as locations suitable for exploration for oil or gas deposits, locations within the geographical area, containing points, from among the plurality of points, having lower earth surface temperatures than points of the plurality of points outside the selected locations.

27. The method of claim 26, including:

selecting points having similar surface features as members of the plurality of points; and measuring the earth surface temperature at each selected point employing an infra-red sensor maintained at about a constant elevation above, and at an angle of about 90 degrees to, the earth's surface at each selected point.

28. The method of claim 27, including:

selecting, as the time period, a time period during which ambient conditions are similar throughout the geographic area.

29. The method of claim 28, including:

maintaining the infra-red sensor at about a constant elevation in the range of about one to four feet above the earth's surface.

30. A method for identifying locations suitable for exploring for oil or gas deposits, which method comprises:

a). selecting a geographic area beneath which oil or gas deposits might be found;

b). selecting a time period during which temperature fluctuations and variations due to topographical, ambient, diurnal and seasonal conditions are minimized;

c). selecting a traverse over at least a portion of the geographic area;

d). measuring an earth surface temperature at each of a plurality of points along the traverse during the selected time period;

e). dividing the plurality of points into a plurality of groups of points wherein the points in each group of points are in linear succession along the traverse;

f). determining an average of the earth surface temperatures measured at the points in each group of points as a group average temperature for each group of points;

g). determining one or more groups of points having a group average temperature lower than group average temperature of other groups of points among the plurality of groups of points; and h). identifying, as an area suitable for exploring for oil or gas deposits, a portion of the traverse containing a group of points having a lower group average temperature than other groups of points along the traverse.

31. The method of claim 30, including:

determining an average of the group average temperatures of the plurality of groups of points as a traverse average temperature;

identifying a group of points having the group average temperature lower than the traverse average temperature; and selecting an area containing the group of points having a group average temperature lower than the traverse average temperature, as a location suitable for exploring for oil or gas deposits.

32. The method of claim 31, including:

measuring the earth surface temperature at each point of the plurality of points employing an infra-red sensor maintained at about a constant elevation above, and at an angle of about 90° to, the surface of the earth.

33. The method of claim 32, including:

selecting a traverse having similar surface features along the traverse.

34. The method of claim 33, including:

selecting a time period during which ambient conditions are similar along the traverse.

35. The method of claim 34, including:

maintaining the infra-red sensor at about a constant elevation in the range of about one to four feet above the earth's surface at each point of the plurality of points.

36. The method of claim 34 including:

selecting as the time period a period of a day after midnight and before dawn.

37. A method for identifying locations suitable for exploring for oil or gas deposits, which method comprising:

a) selecting a geographic area beneath which oil or gas deposits might be found;

b) selecting a time period during which temperature fluctuations and variations due to topographical, ambient, diurnal and seasonal conditions are minimized; including;

c) selecting a traverse over at least a portion of the geographic area;

d) measuring an earth's surface temperature at each of a plurality of points along the traverse;

e) determining an average of the earth's surface temperatures of the plurality of points;

f) identifying, as a location suitable for exploration for oil or gas deposits, adjacent points, of the plurality of points along the traverse, each adjacent point having an earth's surface temperature lower than the average of the earth's surface temperatures of the plurality of points.

* * * * *